(12) United States Patent
Spreitzer et al.

(10) Patent No.: US 6,476,265 B1
(45) Date of Patent: Nov. 5, 2002

(54) METHOD FOR PRODUCING ARYL OLIGOAMINES

(75) Inventors: Hubert Spreitzer, Frankfurt (DE); Willi Kreuder, Mainz (DE); Heinrich Becker, Glashütten (DE); Ute Neumann, Hattersheim (DE)

(73) Assignee: Covion Organic Semiconductors GmbH (DE)

( * ) Notice: Subject to any disclaimer, the term of this patent is extended or adjusted under 35 U.S.C. 154(b) by 0 days.

(21) Appl. No.: 09/486,867

(22) PCT Filed: Aug. 26, 1998

(86) PCT No.: PCT/EP98/05398

§ 371 (c)(1),
(2), (4) Date: May 10, 2000

(87) PCT Pub. No.: WO99/12888

PCT Pub. Date: Mar. 18, 1999

(51) Int. Cl.[7] ............................................. C07C 211/00
(52) U.S. Cl. ..................... 564/307; 564/308; 564/404; 564/405; 564/406; 564/407
(58) Field of Search ................................ 564/307, 308, 564/404, 405, 406, 407

(56) References Cited

U.S. PATENT DOCUMENTS

| 5,576,460 A | 11/1996 | Buchwald et al. | 564/386 |
| 5,831,128 A | 11/1998 | Beller et al. | 564/405 |

FOREIGN PATENT DOCUMENTS

| EP | 0802173 | 10/1997 |
| EP | 0611148 | 6/1998 |
| EP | 0846676 | 6/1998 |

OTHER PUBLICATIONS

Barañano, D., et al, *Current Organic Chemistry* 1:287–305, XP–002085730 (1997).

*Primary Examiner*—Samuel Barts
(74) *Attorney, Agent, or Firm*—Connolly Bove Lodge & Hutz LLP

(57) ABSTRACT

In a process for preparing aryl oligoamines, an amine is reacted with an activated aromatic and a base in a temperature range from 0 to 150° C. in the presence of a palladium component and a phosphine ligand.

The aryl oligoamines are obtained simply and in good yields.

12 Claims, No Drawings

METHOD FOR PRODUCING ARYL OLIGOAMINES

Aryl and heteroaryl derivatives containing a plurality of amine units (hereinafter referred to as aryl oligoamines) have been used in various applications for some time. Thus, they can be employed, for example, as hole conductors in xerography (see, for example, P. M. Borsenberger, D. S. Weiss, Organic Photoreceptors for Imaging Systems, Marcel Dekker, Inc.), in organic electroluminescence devices (see, for example, J. Kido, Bull, Electrochem. 1994, 10, 1–13; DE-A-197 11 714) and dye-sensitized photovoltaic cells (see, for example, DE-A 197 11 714).

Compounds of this type which have attracted particular interest are, inter alia, derivatives of spirobifluorene (see, for example, DE-A 197 11714).

Aryl oligoamines are generally synthesized using variants of the Ullmann reaction (J. March. Adv. Org. Chem. 4th Ed., p. 665, John Wiley & Sons, New York 1992). Thus, the preparation of, for example, 4,4',4"-tris(N,N-diphenylamino)triphenylamine (Shirota et al., Chem. Lett. 1989, 1145–1148) and tris(4-phenoxazin-10-ylphenyl) amine (Higuchi et al., Mol. Cryst. Liq. Cryst. 1994, 242, 127–134) by this route has been described. This reaction has also been described for producing hole conductors based on spiro compounds such as N,N,N',N',N",N",N'",N'"-octaphenylspiro-9,9'-bifluorene-2,2',7,7'-tetramine (Salbeck et al., Book of Abstracts, 213th ACS National Meeting, San Francisco 1997, 199).

It is generally the case that the preparation of aryl oligoamines is associated with increased difficulties compared to that of aryl monoamines. Thus, for example, it is known that Ullmann reactions can be carried out at a yield of about 80% under optimum conditions. If this is then assumed for each step of a tri-coupling or tetra-coupling reaction, the calculated yield is then only 51 or 41%, which firstly has an adverse effect on the economy and secondly makes it more difficult to purify the products.

It has surprisingly been found that aryl oligoamines can be prepared simply and in good yields by direct coupling of a primary or secondary amine with an activated aromatic in the presence of a base, a palladium component and a phosphine ligand.

Although a similar process is known from U.S. Pat. No. 5,576,460, that document describes only the preparation of aryl monoamines. In addition, a yield of merely 75% is obtained in the sole example, from which a person skilled in the art would conclude that such a method is less suitable than the Ullmann reaction for building up aryl oligoamines.

The invention accordingly provides a process for preparing aryl oligoamines, which comprises reacting an amine with an activated aromatic and a base in a temperature range from 0 to 150° C. in the presence of a palladium component and a phosphine ligand.

For the purposes of the present invention, an aryl oligoamine is a compound which contains at least two amine units bound to aromatic groups.

Preferred starting compounds are activated aromatics of the formula (I), $$(R)_n - A - (X)_m \quad (I)$$

where the symbols and indices have the following meanings:

A is an aromatic and/or heteroaromatic radical which has from 2 to 200 carbon atoms and can contain a plurality of aromatic and/or heteroaromatic groups, where such groups are then fused (for example anthracene, triphenylene) or unfused (for example biphenyl, terphenyl, 1,3,5-triphenylbenzene);

R are identical or different and are each $NO_2$, CN, F, an unbranched or branched alkyl group having from 1 to 22 carbon atoms, where one or more $CH_2$ groups may be replaced by —O—, —S—, —CO—, —O—CO—, —CO—O—, —O—CO—O—, —$CR^1$=$CR^2$—, —C≡C—, $SiR^3R^4$, $C_4$–$C_{10}$-aryldiyl, $C_4$–$C_{10}$-heteroaryldiyl, cyclohexylene, —$NR^5$—, where heteroatoms must not be directly bonded to one another, and where one or more H atoms may be replaced by F, Cl, Br;

$R^1$, $R^2$ are identical or different and are H, CN, $C_1$–$C_{12}$-alkyl, $C_4$–$C_{10}$-aryl;

$R^3$, $R^4$ are identical or different and are $C_1$–$C_{12}$-alkyl, $C_4$–$C_{10}$-aryl;

$R^5$ is $C_1$–$C_{12}$-alkyl, $C_4$–$C_{10}$-aryl;

X is Cl, Br, I, mesylate, tosylate or $C_1$–$C_{12}$-perfluoroalkylsulfonate;

m is a natural number and $2 \leq m \leq y$;

n is a natural number and $0 \leq n \leq y-m$;

y is the number of free valences on the parent unit A.

The symbols and indices in the formula (I) preferably have the following meanings:

R are identical or different and are each $NO_2$, CN, F, an unbranched or branched alkyl group having from 1 to 22 carbon atoms;

X is Cl, Br, I, tosylate;

m is such that $3 \leq m \leq y$.

The symbols and indices in the formula (I) particularly preferably have the following meanings:

A is benzene, naphthalene, anthracene, pyrene, triphenylene, biphenyl, fluorene, terphenyl, 1,3,5-triphenylbenzene, spiro-9,9'-bifluorene, 2,2',7,7'-tetraphenylspiro-9,9'-bifluorene, 2,2',7,7'-tetra(4'-biphenylyl)spiro-9,9'-biphenyl, 2,4,7,2',4',7'-hexaphenylspiro-9,9'-bifluorene or 2,4,7,2',4',7'-hexa(4'-biphenylyl)spiro-9,9'-bifluorene or another oligophenylene-substituted derivative of spiro-9,9'-bifluorene;

R are identical or different and are each $NO_2$, CN, F, an unbranched or branched alkyl group having from 1 to 22 carbon atoms;

X is Br, I;

m is 4, 5 or 6 and n is 0, 1, 2, 3, 4, 5, 6.

Very particularly preferred activated aromatics of the formula (I) are those of the formula (Ia)

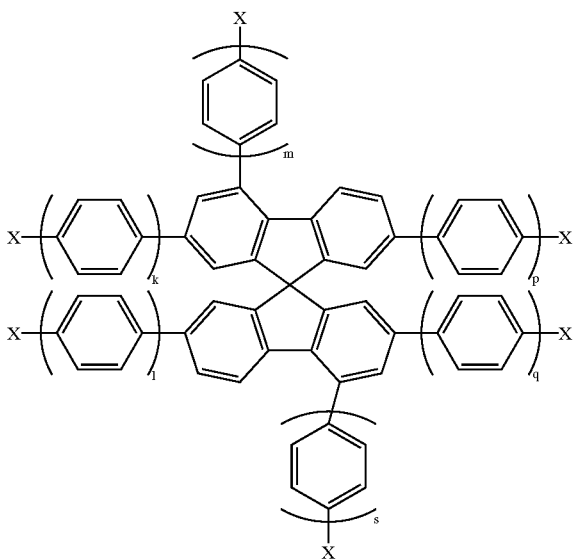

(Ia)

where

X are identical or different and are each Br, I or H and k,l,p,q,r,s are 0, 1, 2, 3, 4, with the proviso that at least two, preferably at least four, of the radicals X are Br or I.

Preferred amine components are those of the formula (II),

$H-NR^7R^8$ (II)

where the symbols have the following meanings:

$R^7, R^8$ are identical or different and are each a) H;

b) a straight-chain, branched or cyclic alkyl group having from 1 to 22 carbon atoms, where one or more $CH_2$ groups may be replaced by —O—, —S—, —CO—, —OCO—, —CO—O—, —O—CO—O—, —$CR^1$=$CR^2$—, —C≡C—, $SiR^3R^4$, $C_4$–$C_{10}$-aryldiyl, $C_4$–$C_{10}$-heteroaryldiyl, cyclohexylene, —$NR^5$—, where heteroatoms must not be directly bonded to one another, and where one or more H atoms may be replaced by F, Cl, Br; where $R^1$ to $R^5$ are as defined in the formula (I);

c) a $C_4$–$C_{12}$-aryl or heteroaryl group which may be substituted by one or more radicals R, where R are identical or different and are as defined in the formula (I).

End products of the process of the invention and their preferences may be derived from the starting materials and their preferences.

The starting materials for the process are known in principle and are either commercially available or can be prepared by known methods with which those skilled in the art are familiar, for example as described in Houben-Weyl, Methoden der Organischen Chemie, Georg Thieme Verlag, Stuttgart.

The ratio of the starting materials is not critical and can therefore be varied within a wide range; preference is given to a ratio of activated group to amine of 1:0.8–2, particularly preferably 1:1–1.5.

According to the invention, the starting compounds, viz. amine and activated aromatic, are reacted in a coupling reaction to form an aryl oligoamine. To carry out the reaction, the amine, the activated aromatic, a base and catalytic amounts of a palladium catalyst containing phosphine ligands or a palladium salt and a phosphine are taken up in a solvent and reacted at a temperature of from 0° C. to 150° C., preferably from 30° C. to 140° C., particularly preferably from 50° C. to 120° C., very particularly preferably from 80° C. to 120° C., for a time of from 1 hour to 200 hours, preferably from 5 hours to 100 hours, particularly preferably from 10 hours to 80 hours. The work-up is carried out by methods which are known per se and with which those skilled in the art are familiar, for example by hydrolysis, stirring with a solvent, phase separation and removal of the solvent. Preferably, the palladium component is also removed by stirring with a complexing agent. Complexing agents which are suitable here are, inter alia, cyanide, thiocyanate and the like. The crude product can then be purified by methods with which tho se skilled in the art are familiar and which are appropriate for the respective product, e.g. by recrystallization, distillation, sublimation, zone melting, melt crystallization or chromatography.

The process of the invention is generally carried out in a solvent; an excess of the base or a starting material, preferably the amine component, can also serve as such a solvent.

Preference is given to using one or more organic solvents or a mixture of water and one or more organic solvents, in which case preferably at least one of the organic solvents should be insoluble in water. Preferred organic solvents are ethers, e.g. diethyl ether, dimethoxymethane, diethylene glycol dimethyl ether, tetrahydrofuran, dioxane, dioxolane, diisopropyl ether, tert-butyl methyl ether, hydrocarbons, e.g. hexane, isohexane, heptane, cyclohexane, toluene, xylene, alcohols, e.g. methanol, ethanol, 1-propanol, 2-propanol, ethylene glycol, 1-butanol, 2-butanol, tert-butanol, ketones, e.g. acetone, ethyl methyl ketone, isobutyl methyl ketone, amides, e.g. dimethylformamide, dimethyl acetamide, N-methylpyrrolidone, nitriles, e.g. acetonitrilie, propionitrile, butyronitrile, and mixtures thereof.

Particularly preferred organic solvent s are ether s such as dimethoxyethane, diethylene glycol dimethyl ether, tetrahydrofuran, dioxane or diisopropyl ether, hydrocarbons such as hexane, heptane, cyclohexane, toluene or xylene, alcohols such as methanol, ethanol, 1-propanol, 2-propanol, 1-butanol, 2-butanol, tert-butanol or ethylene glycol, ketones such as methyl ethyl ketone or isobutyl methyl ketone, amides such as dimethylformamide, dimethylacetamide or N-methylpyrrolidone, and mixtures thereof.

Very particularly preferred organic solvents are ethers, e.g. dimethoxyethane, tetrahydrofuran, dioxane, hydrocarbons, e.g. cyclohexane, toluene, xylene, alcohols, e.g. ethanol, 1-propanol, 2-propanol, 1-butanol, tert-butanol and mixtures thereof.

Examples of the use of water and organic solvents are mixtures of water and toluene or of water, toluene and tetrahydrofuran.

Bases which are preferably used in the process of the invention are alkali metal and alkaline earth metal hydroxides, alkali metal and alkaline earth metal carbonates, alkali metal hydrogencarbonates, alkali metal and alkaline earth metal acetates, alkali metal and alkaline earth metal alkoxides, and also primary, secondary and tertiary amines. This means that the amine component used can also act as base, given an appropriate excess. Particular preference is given to alkali metal and alkaline earth metal hydroxides, alkali metal and alkaline earth metal carbonates and alkali metal and alkaline earth metal alkoxides. Very particular preference is given to alkali metal hydroxides such as sodium hydroxide and potassium hydroxide, and to alkali metal and alkaline earth metal alkoxides such as sodium ethoxide and sodium or potassium tert-butoxide.

In the process of the invention, the base is preferably used in an amount of from 50 to 500 mol %, particularly preferably from 50 to 250 mol %, very particularly preferably from 75 to 200 mol %, in particular from 90 to 120 mol %, based on the number of mol of N-H present.

The palladium component comprises palladium metal or a palladium(0) or (II) compound.

Palladium component and phosphine ligand can be used as a complex, e.g. as the advantageous $Pd(PPh_3)_4$, or separately.

Suitable palladium components are, for example, palladium compounds such as palladium ketonates, palladium acetylacetonates, nitrilepalladium halides, olefinpalladium halides, palladium halides, allylpalladium halides and palladium biscarboxylates, preferably palladium ketonates, palladium acetylacetonates, bis-$\eta^2$-olefinpalladium dihalides, palladium(II) halides, $\eta^3$-allylpalladium halide dimers and palladium biscarboxylates, very particularly preferably bis (dibenzylideneacetone)palladium(0) [$Pd(dba)_2$)], $Pd(dba)_2$ $CHCl_3$, palladium bisacetylacetonate, bis(benzonitrile) palladium dichloride, $PdCl_2$, $Na_2PdCl_4$, dichlorobis (dimethyl sulfoxide)palladium(II), bis(acetonitrile) palladium dichloride, palladium(II) acetate, palladium(II) propionate, palladium(II) butanoate and (1c,5c-cyclooctadiene)palladium dichloride.

Another palladium component which can likewise be used is palladium in metallic form, hereinafter referred to simply as palladium, preferably palladium in powder form or on a support material, e.g. palladium on activated carbon, palladium on aluminum oxide, palladium on barium carbonate, palladium on barium sulfate, palladium on aluminum silicates such as montmorillonite, palladium on $SiO_2$ and palladium on calcium carbonate, each having a palladium content of from 0.5 to 10% by weight. Particular preference is given to palladium in powder form, palladium on activated carbon, palladium on barium carbonate and/or calcium carbonate and palladium on barium sulfate, each having a palladium content of from 0.5 to 10% by weight. Very particular preference is given to palladium on activated carbon having a palladium content of 5 or 10% by weight.

In the process of the invention, the palladium component is used in an amount of from 0.01 to 10 mol %, preferably from 0.05 to 5 mol %, particularly preferably from 0.1 to 3 mol %, very particularly preferably from 0.1 to 1.5 mol %, based on N—H groups present.

Phosphine ligands which are suitable for the process of the invention are, for example, trialkylphosphines, tricycloalkylphosphines, triarylphosphines, where the three substituents on the phosphorus may be identical or different, chiral or achiral and one or more of the ligands may link the phosphorus groups of a plurality of phosphines, where part of this linkage may also be one or more metal atoms. Examples of phosphines which can be used in the process of the invention are trimethylphosphine, tributylphosphine, tricyclohexylphosphine, triphenylphosphine, tritolylphosphine, tris(4-dimethylamino-phenyl)phosphine, bis(diphenylphosphino)methane, 1,2-bis (diphenylphosphino)ethane, 1,3-bis(diphenylphosphino) propane and 1,1'-bis(diphenylphosphino)ferrocene.

Very particular preference is given to triphenylphosphine, tris(o-tolyl)phosphine, 1,2-bis(diphenylphosphino)ethane, 1,3-bis(diphenyl-phosphino)propane and 1,1'-bis (diphenylphosphino)ferrocene, in particular triphenylphosphine and tris(o-tolyl)phosphine.

Further phosphine ligands which are suitable for the process of the invention are water-soluble phosphine ligands which contain, for example, sulfonate salt and/or sulfonic acid groups and/or carboxylate salt and/or carboxyl groups and/or phosphonate salt and/or phosphonic acid groups and/or phosphonium groups and/or peralkylammonium groups and/or hydroxy groups and/or polyether groups having a suitable chain length.

Preferred classes of water-soluble phosphine ligands are trialkylphosphines, tricycloalkylphosphines, triarylphosphines, dialkylarylphosphines, alkyldiarylphosphines and heteroarylphosphines, e.g. tripyridylphosphine and trifurylphosphine, substituted by the above groups, where the three substituents on the phosphorus may be identical or different, chiral or achiral and one or more of the ligands may link the phosphorus groups of a plurality of phosphines, where part of this linkage can also be one or more metal atoms.

In the process of the invention, the phosphine ligand is used in an amount of from 0.1 to 20 mol %, preferably from 0.2 to 15 mol %, particularly preferably from 0.5 to 10 mol %, very particularly preferably from 1 to 6 mol %, based on N—H groups present. It is also possible, if desired, to use mixtures of two or more different phosphine ligands.

The products of the process of the invention are suitable, for example, for use in electroluminescence devices, dye-sensitized photovoltaic cells or in xerography, for example as hole conductor materials.

The invention is illustrated by the following examples without being restricted thereby.

EXAMPLE 1

Preparation of 2,2',7,7'-tetrakis(N,N-diphenylamino) spiro-9,9'-bifluorene 2,2',7,7'-Tetrabromo-9,9'-spirobifluorene (20.86 g, 33 mmol) and diphenylamine (25.38 g, 150 mmol) were dissolved in toluene (400 ml) and the solution was saturated with $N_2$. $Pd(OAC)_2$ (311 mg, 1.5 mmol), $P(o-tolyl)_3$ (0.913 g, 3 mmol) and the base (NaO$^t$Bu, 20.18 g, 210 mmol) were subsequently added. The solution immediately became dark green. It was stirred under reflux for 72 hours. After cooling the mixture to room temperature, NaCN solution was added (about 2 g of NaCN in 200 ml of water) and the mixture was stirred for about 60 minutes. The organic phase was subsequently washed three times with water. The organic phase was dried over $Na_2SO_4$ and the solvent was then taken off. This gave light-brown crystals. These were recrystallized from 100 ml of dioxane and 5 ml of hydrazine hydrate. This procedure was repeated once. Finally, the crystals obtained were stirred with hexane a number of times and dried at 60° C. under reduced pressure. This gave 19.3 g (59%) of colorless powder which, according to HPLC, had a purity of greater than 99.7%.

$^1$H NMR (CDCl$_3$, NH$_2$NH$_2$*H2O): δ [ppm]=7.45 (d, 4H, H-4, J=8 Hz), 7.19 (m, 16 H, H-3'), 6.97 (m, 24 H, H-2', H4'), 6.92 (dd, 4 H, H-3, J$_1$=2, J$_2$=8 Hz), 6.69 (d, 4 H, H-1, J=2 Hz).

The use of DPPF (bis(diphenylphosphino)ferrocene) as ligand led to a deterioration in yield (45%; purity: >99.9%), but the use of BINAP (2,2'-bis(diphenylphosphino)-1,1'-binaphthyl) led to a slight increase in yield (62%; purity: >99.7%).

EXAMPLE 2

Preparation of 2,2',7,7'-tetrakis(N,N-di4-methoxyphenylamino)spiro-9,9'-bifluorene 2,2',7,7'-Tetrabromo-9,9'-spirobifluorene (13.9 g, 22 mmol) and 4,4'-dimethoxydiphenylamine (22.98 g, 100 mmol) were dissolved in toluene (250 ml) and the solution was saturated with $N_2$. The solution became brown. $Pd(OAc)_2$ (223 mg, 1 mmol) and $P(o\text{-tolyl})_3$ (608 mg, 2 mmol) were subsequently added. $NaO^tBu$ (13.5 g, 140 mmol) was added dropwise as a solution in dioxane (in 150 ml). The solution slowly became dark brown during the dropwise addition. The solution was stirred under reflux for 72 hours under protective gas.

After cooling to room temperature, the mixture was hydrolyzed with $H_2O$, the aqueous phase was separated off, the organic phase was stirred with NaCN solution (3 g of NaCN in 300 ml of water) for 2 hours and the aqueous phase was subsequently separated off again. The organic phase was filtered and the solvent was taken off. This gave a black oil which solidified after some time. It was dissolved in 50 ml of hot dioxane, admixed hot with 50 ml of ethanol and cooled whilst stirring. This resulted in precipitation of a yellow-green solid. This was filtered off with suction and washed a number of times with small portions (each 2 ml) of dioxane until the color was light yellow. It was subsequently recrystallized from a very small amount of dioxane (addition of a few drops of hydrazine hydrate). This gave 13.9 g (52%) of virtually colorless powder which, according to $^1$H-NMR, had a purity of 99%.

$^1$H NMR (CDCl$_3$, NH$_2$NH$_2$*H$_2$O): δ [ppm]=7.36 (d, 4H, H-4, J=8 Hz), 6.90+6.75 (AA'BB', each 16 H, H-2', H-3'), 6.79 (dd, 4 H, H-3, $J_1$=2, $J_2$=8 Hz), 6.55 (d, 4 H, H-1, J=2 Hz), 3.77 (s, 24 H, OMe).

EXAMPLE 3

Preparation of 2,2',7,7'-tetrakis(N-phenothiazinyl) spiro-9,9'-bifluorene

The reaction was carried out using a method analogous to Example 2. In the work-up, the solid formed after stirring with NaCN solution was filtered off with suction. The resulting solid was first extracted with boiling acetone:water:hydrazine hydrate (70:15:3) for about 1 hour and finally recrystallized from chloroform:ethanol (1:1). This gave the pure product (purity>99% according to H-NMR) as a colorless powder; 47% yield.

$^1$H NMR (CDCl$_3$, NH$_2$NH$_2$*H$_2$O): δ [ppm]=8.06 (d, 4H, H-4, J=8 Hz), 7.43 (dd, 4 H, H-3, $J_1$=2, $J_2$=8 Hz), 7.08 (d, 4 H, H-1, J=2 Hz), 6.96 (dd, 4 H, H-4', $J_1$=1.5, $J_2$=7.5 Hz), 6.71 (dt, 4 H, H-3', $J_1$=1.2, $J_2$=7.5 Hz), 6.47 (ddd, 4 H, H-2', $J_1$=1.5, $J_2$=7.3 Hz, $J_3$=8.3 Hz), 5.98 (dd, 4 H, H-1', $J_1$=1.0, $J_2$=8.3 Hz).

EXAMPLE 4

Preparation of 2,2',7,7'-tetrakis(N,N-di-4-methylphenylamino)spiro-9,9'-bifluorene 2,2',7,7'-Tetrabromo-9,9'-spirobifluorene and 4,4'-dimethyidiphenylamine were reacted using a method analogous to Example 2. The work-up was likewise carried out analogously. After drying, 51% of product was obtained purity: >99.5% according to NMR). $^1$H NMR (CDCl$_3$, NH$_2$NH$_2$H*$_2$O): δ [ppm]=7.39 (d, 4H, H-4, J=8 Hz), 6.99+6.88 (AA'BB', each 16 H, H-2', H-3'), 6.85 (dd, 4 H, H-3, $J_1$=2, $J_2$=8 Hz), 6.66 (d, 4 H, H-1, J=2 Hz), 2.29 (s, 24 H, Me).

EXAMPLE 5

Preparation of 2,2',7,7'-tetrakis(N-phenyl-N-(3-methylphenylamino)spiro-9,9'-bifluorene 2,2',7,7'-Tetrabromo-9,9'-spirobifluorene and 3-methyldiphenylamine were reacted using a method analogous to Example 1. DPPF was used as ligand. The work-up was likewise carried out analogously, but the product proved to be significantly more difficult to purify. It was therefore first filtered twice through a silica gel column and subsequently recrystallized first from ethyl acetate/methanol (2:1) and then a number of times from dioxane. After drying, 26% of product was obtained (purity: >99.9% according to HPLC).

$^1$H NMR (CDCl$_3$, NH$_2$NH$_2$*H$_2$O): δ [ppm]=7.43 (d, 4H, H-4, J=8 Hz), 7.18+6.97+6.94 (AA'BB'C, 8+8+4 H, H-3', H-2', H-4'), 7.08 (t, 4 H, H-5", J=7 Hz), 6.89 (dd, 4 H, H-3, $J_1$=2, $J_2$=8 Hz), 6.84 (s (br), 4 H, H-2") 6.78 (m, 8 H, H-4", H-6"), 6.68 (d, 4 H, H-1, J=2 Hz), 2.22 (s, 12 H, Me).

EXAMPLE 6

Preparation of 2,2',7,7'-tetrakis(N,N-di4-biphenylamino)spiro-9,9'-bifluorene 2,2',7,7'-Tetrabromo-9,9'-spirobifluorene and 4,4'-biphenylamine were reacted using a method analogous to Example 2. The work-up was likewise carried out analogously. After drying, 31% of product was obtained (purity: >99.7% according to HPLC). $^1$H NMR (CDCl$_3$, NH$_2$NH$_2$*H$_2$O): δ [ppm] =7.53 (d, 4H, H-4, J=8 Hz), 7.51+7.37+7.28 (M'BB'C, 16+16+8 H, H-2", H-3", H-4"), 7.42+7.12 (AA'BB', each 16 H, H-2', H-3'), 7.03 (dd, 4 H, H-3, $J_1$=2, $J_2$=8 Hz), 6.86 (d, 4 H, H-1, J=2 Hz).

EXAMPLE 7

Preparation of 2,2',7,7'-tetrakis(N-phenyl-N-(2-naphthylamino)spiro-9,9'-bifluorene 2,2',7,7'-Tetrabromo-9,9'-spirobifluorene and 2-naphthylphenylamine were reacted using a method analogous to Example 5. The work-up was likewise carried out analogously; the product likewise proved to be difficult to purify. It was therefore first filtered twice through a silica gel column, and then recrystallized a number of times from dioxane/methanol. After drying, 35% of product was obtained (purity: >99.7% according to HPLC).

$^1$H NMR (CDCl$_3$, NH$_2$NH$_2$*H$_2$O): δ [ppm]=7.75 (dd, 4 H, H-5$_{NP}$, $J_1$=2, $J_2$=7 Hz), 7.67 (d, 4 H, H-4$_{NP}$, J=9 Hz), 7.53 (dd, 4 H, H-8$_{NP}$, $J_1$=2, $J_2$ =7.5 Hz), 7.44 (d, 4H, H-4, J=8 Hz), 7.35 (m, 12 H, H-1$_{NP}$, H-6$_{NP}$, H-7$_{NP}$), 7.23+7.08+7.03 (AA'BB'C, 8+8+4 H, H-3$_{PH}$, H-2$_{PH}$, H-4$_{PH}$), 7.19 (dd, 4 H, H-3$_{NP}$, $J_1$=2, $J_2$=8.8 Hz), 6.95 (dd, 4 H, H-3, $J_1$=2, $J_2$=8 Hz), 6.76 (d, 4 H, H-1, J=2 Hz).

What is claimed is:

1. A process for preparing aryl oligoamines, which comprises reacting an amine with an activated aromatic and a base in a temperature range from 0 to 150° C. in the presence of a palladium component and a phosphine ligand.

2. The process as claimed in claim 1, wherein the activated aromatic used is a compound of the formula (I),

$$(R)_n-A-(X)_m \quad (I)$$

where the symbols and indices have the following meanings:

A is an aromatic and/or heteroaromatic radical which has from 2 to 200 carbon atoms and can contain a plurality of aromatic and/or heteroaromatic groups, where such groups are then fused;

R are identical or different and are each NO$_2$, CN, F, an unbranched or branched alkyl group having from 1 to 22 carbon atoms, where one or more CH$_2$ groups may be replaced by —O—, —S—, —CO—, —O—CO—, —CO—O—, —O—CO—O—, —CR$^1$=CR$^2$, —C≡C—, SiR$^3$R$^4$, C$_4$–C$_{10}$-aryldiyl, C$_4$–C$_{10}$-heteroaryldiyl, cyclohexylene, —NR$^5$—, where heteroatoms must not be directly bonded to one another, and where one or more H atoms may be replaced by F, Cl, Br;

R$^1$, R$^2$ are identical or different and are H, CN, C$_1$–C$_{12}$-alkyl, C$_4$–C$_{10}$-aryl;

R$^3$, R$^4$ are identical or different and are C$_1$–C$_{12}$-alkyl, C$_4$–C$_{10}$-aryl;

R$^5$ is C$_1$–C$_{12}$-alkyl, C$_4$–C$_{10}$-aryl;

X is Cl, Br, I, mesylate, tosylate or C$_1$–C$_{12}$-perfluoroalkylsulfonate;

m is a natural number and $2 \leq m \leq y$;

n is a natural number and $0 \leq n \leq y-m$;

y is the number of free valences on the parent unit A.

3. The process as claimed in claim 2, wherein the activated aromatic used is a compound of the formula (Ia),

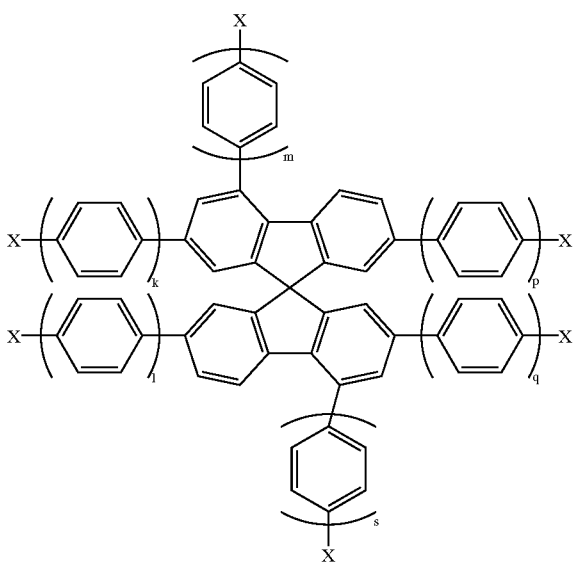

(Ia)

where

X are identical or different and are each Br, I or H and k, l, p, q, r, s are 0, 1, 2, 3, 4, with the proviso that at least two of the radicals X are Br or I.

4. The process as claimed in one or more of the preceding claims, wherein the amine component used is a compound of the formula (II),

(II)

where the symbols have the following meanings:

R$^7$, R$^8$ are identical or different and are each
  a) H;
  b) a straight-chain, branched or cyclic alkyl group having from 1 to 22 carbon atoms, where one or more CH$_2$ groups may be replaced by —O—, —S—, —CO—, —OCO—, —CO—O—, —O—CO—O—, —CR$^1$=CR$^2$, —C≡C—, SiR$^3$R$^4$, C$_4$–C$_{10}$-aryldiyl, C$_4$–C$_{10}$-heteroaryldiyl, cyclohexylene, —NR$^5$—, where heteroatoms must not be directly bonded to one another, and where one or more H atoms may be replaced by F, Cl, Br; where R$^1$ to R$^5$ are as defined in the formula (I) in claim 2;
  c) a C$_4$–C$_{12}$-aryl or heteroaryl group which may be substituted by one or more radicals R, where R are identical or different and R as defined in the formula (I) in claim 2.

5. The process as claimed in one or more of the preceding claims, wherein a base selected from the group consisting of alkali metal and alkaline earth metal hydroxides, alkali metal and alkaline earth metal carbonates, alkali metal hydrogencarbonates, alkali metal and alkaline earth metal acetates, alkali metal and alkaline earth metal alkoxides and primary, secondary and tertiary amines is used.

6. The process as claimed in one or more of the preceding claims, wherein the palladium component used is palladium metal, a palladium compound or a palladium complex containing a phosphine ligand.

7. The process as claimed in one or more of the preceding claims, wherein a phosphine ligand selected from the group consisting of trialkylphosphines, tricycloalkylphosphines and triarylphosphines, where the three substituents on the phosphorus may be identical or different, chiral or achiral and one or more of the ligands may link the phosphorus groups of a plurality of phosphines, where part of this linkage may also be one or more metal atoms, is used.

8. The process as claimed in claim 1, wherein the ratio of activated group on the aromatic to amine is 1:1–1.5.

9. The process as claimed in claim 1, wherein the palladium component is used in an amount of from 0.01 to 10 mol % based on N—H groups present.

10. The process as claimed in claim 1, wherein the palladium component is used in an amount of from 0.05 to 5 mol % based on N—H groups present.

11. The process as claimed in claim 1, wherein the palladium component is used in an amount of from 0.1 to 3 mol % based on N—H groups present.

12. The process as claimed in claim 1, wherein the palladium component is used in an amount of from 0.1 to 1.5 mol % based on N—H groups present.

* * * * *

UNITED STATES PATENT AND TRADEMARK OFFICE
CERTIFICATE OF CORRECTION

PATENT NO.    : 6,476,265 B1
DATED         : November 5, 2002
INVENTOR(S)   : Spreitzer et al.

It is certified that error appears in the above-identified patent and that said Letters Patent is hereby corrected as shown below:

<u>Column 9,</u>
Lines 49-50, delete "one or more of the preceding claims" and insert -- claim 2 --.

<u>Column 10,</u>
Lines 19-20, delete "one or more of the preceding claims" and insert -- claim 1 --.
Lines 26-27, delete "one or more of the preceding claims" and insert -- claim 1 --.
Lines 30-31, delete "one or more of the preceding claims" and insert -- claim 1 --.

Signed and Sealed this

Eighth Day of April, 2003

JAMES E. ROGAN
*Director of the United States Patent and Trademark Office*